US009119379B1

(12) United States Patent
Yancey et al.

(10) Patent No.: US 9,119,379 B1
(45) Date of Patent: Sep. 1, 2015

(54) SYSTEMS AND METHODS FOR DETECTING ESTRUS

(71) Applicants: William B. Yancey, Denver, CO (US); Linda C. Frank, Denver, CO (US); Bruce E. Johnson, Denver, CO (US)

(72) Inventors: William B. Yancey, Denver, CO (US); Linda C. Frank, Denver, CO (US); Bruce E. Johnson, Denver, CO (US)

(*) Notice: Subject to any disclaimer, the term of this patent is extended or adjusted under 35 U.S.C. 154(b) by 159 days.

(21) Appl. No.: 13/573,769

(22) Filed: Oct. 4, 2012

(51) Int. Cl.
*A61D 17/00* (2006.01)
*A61B 10/00* (2006.01)
*A01K 29/00* (2006.01)
*A61B 5/00* (2006.01)

(52) U.S. Cl.
CPC ............. *A01K 29/005* (2013.01); *A61B 5/0004* (2013.01); *A61B 5/4368* (2013.01); *A61B 10/0012* (2013.01); *A61D 17/002* (2013.01); *A61D 17/004* (2013.01)

(58) Field of Classification Search
CPC . A61D 17/002; A61D 17/004; A01K 29/005; A61B 10/0012
USPC .................................................. 600/551, 549
See application file for complete search history.

(56) References Cited

U.S. PATENT DOCUMENTS

| 4,895,165 | A | * | 1/1990 | Blair .............................. 600/551 |
| 5,111,799 | A | * | 5/1992 | Senger et al. ................. 600/551 |
| 5,216,599 | A | * | 6/1993 | Uebe et al. .................... 600/551 |
| 5,542,431 | A | * | 8/1996 | Starzl et al. ................... 600/551 |
| 5,881,673 | A | * | 3/1999 | Beach et al. .................. 119/174 |
| 6,236,318 | B1 | * | 5/2001 | Yang et al. ................. 340/573.3 |
| 7,137,359 | B1 | * | 11/2006 | Braden ......................... 119/854 |
| 2003/0120173 | A1 | * | 6/2003 | Saini et al. .................... 600/551 |
| 2008/0110406 | A1 | * | 5/2008 | Anderson et al. ............. 119/174 |
| 2008/0204255 | A1 | * | 8/2008 | Flexer et al. ............... 340/573.7 |
| 2008/0236500 | A1 | * | 10/2008 | Hodges et al. ............. 119/14.02 |
| 2010/0030036 | A1 | * | 2/2010 | Mottram et al. .............. 600/301 |
| 2010/0300462 | A1 | * | 12/2010 | Ardrey, Jr. .................... 128/899 |

OTHER PUBLICATIONS

Kamphuis et al. Field evaluation of 2 collar-mounted activity meters for detecting cows in estrus on a large pasture-grazed dairy farm: J. Dairy Sci. 95:3045-3056 Jun. 2012.*
Valenza et al. "Assessment of an accelerometer system for detection of estrus and tratment with gonadotropin-releasing hormone at the timeof insemination in lactating dairy cows" J. Dairy Sci. 95:7115-7127 No. 12. E-Published online Oct. 3, 2012.*

* cited by examiner

*Primary Examiner* — Sean Dougherty
*Assistant Examiner* — Michael C Stout
(74) *Attorney, Agent, or Firm* — Skinner and Associates; Joel Skinner

(57) ABSTRACT

Methods, devices, and systems are provided for identifying estrus or onset of estrus in a female animal.

25 Claims, 14 Drawing Sheets

☐ RECEIVER SETUP      _ ☐ ✕

FILE   DIAGNOSTICS

┌─ RECEIVERS: ─────────────────────────┐ ┌─ SERVER INFORMATION ──────────────────┐
| ID   | MODEL              | PORT |
|------|--------------------|------|
| 8712 | ACCUBREED – E4000  | COM1 |
| 2401 | HEATWATCH 1 – RCVR | COM4 |

SERVER:   HTTP://127.0.0.1/
PORT:   8080
AUTHKEY:   {2862B44A-1073dc-A41E-41557810
MYID:   8712

TEST SETTINGS

┌─ RECEIVER ──────────────────────────┐
MODEL:   ACCUBREED – E4000 ▶
COM PORT:   COM1 ▶

AUTO DETECT

ADD     DELETE

FIG. 16

SYSTEMS AND METHODS FOR DETECTING ESTRUS

CROSS REFERENCE TO RELATED APPLICATIONS, IF ANY

This application claims the benefit under 35 U.S.C. §119(e) of U.S. Provisional Patent Application Ser. No. 61/543,728, filed Oct. 5, 2011, which is hereby incorporated by reference.

37 C.F.R. §1.71(E) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Technical Field

The invention provides methods and systems for detecting estrus in animals, and in particular, methods and systems for determining optimal breeding time in a female animal.

2. Background

Accurate determination of estrus in cattle and other animals, including both domestic animals and wildlife, is an economically important procedure in the field of animal husbandry. An accurate estrus determination identifies the window of time in which the animal can be inseminated. In cattle, the estrous period occurs approximately every 21 days in non-pregnant females and usually lasts only about twelve to eighteen hours with peak estrus being about six hours in duration. With many animals active nocturnally, including cattle, the relatively short duration of peak estrus period can be difficult to detect without a reliable automated monitoring system. A failure to achieve pregnancy in the cycling animal can be costly, particularly in terms of production or missed opportunity.

There are several observable signs indicating that an animal is in estrus (heat). Of particular importance, females of various animal species such as domestic cows will permit themselves to be mounted by other females which may or may not be in estrus. If a mounted female allows the mount to continue for more than a few seconds, then the mounted female is likely in estrus. Although females may be mounted at times outside of estrus, females will allow themselves to be heat mounted for relatively prolonged times. When an animal is not in estrus, she will try to move out from under a mount (a false mount or false positive). Direct observation is the most common method of determining whether an animal is in heat during these episodes.

Available systems for estrus detection may require implantation of devices into the tailhead of females to sense mounting events. The use of implants presents several difficulties including the need for surgical placement, possibilities for infection from implantation, and the problem of replacing defective or damaged implanted components.

Other systems for detecting estrus provide for a visible display on the body of the female, e.g. when a mount occurs (standing or false) a colored liquid is released onto the tailhead of the mounted animal. Such systems have limited utility because estrus monitoring information is limited to visual inspection of the female. The rancher or breeder must go to a location within sight of the females in order to determine which females are in estrus. Given the short duration of estrus in most animals, this poses a significant inconvenience to the rancher and adds potential for missing the estrus even where the rancher or breeder is well intentioned. In addition, there is no indication as to whether any mount episode was associated with an animal in estrus.

Still other systems include pedometers to measure activity of the animal or vaginal probes to measure chemical changes in the vagina as the animal approaches ovulation.

However, most estrus detecting systems have a high rate of false positive estrus determinations. For example, a mounting female may maintain an extended mount even when the mounted female is not in estrus and thus is trying to move away from the mount.

Female domestic animals, particularly cows, are more physically active during estrus than at other times. This increased activity may include walking, running, and attempts to mount other animals. Increased activity amplifies the number of false positives determined by existing methods for detecting estrus.

Therefore, there is a need in the art to provide new methods and systems for detecting estrus.

Provided herein are methods and systems directed toward overcoming one or more of the problems discussed above.

BRIEF SUMMARY OF THE INVENTION

Provided herein are systems, devices, and methods for detecting and identifying an animal in estrus.

For example, provided herein are systems for determining estrus in a female animal. Such a system comprises
  (a) a hermetically sealed housing enclosing a radio transmitter, a pressure switch, an encoder, an accelerometer, a circuit board, an antenna, and a battery, wherein the housing and its contents are reusable or disposable;
  (b) a transceiver comprising a tuner, a power source, an antenna, and a cellular (analog or digital), Radio Frequency (RF), Wi-Fi Wireless, or combination link; and
  (c) a central server;
wherein the data generated by activation of the pressure switch is sent from the transmitter to the transceiver and then from the transceiver to the central server where a determination of estrus is made by a user or by software accessed by a user.

In some aspects, the system further comprises one or more repeaters and/or one or more data entry devices.

In some aspects, the system further includes a GPS transmitter, a counter, a temperature sensor, and/or a humidity sensor.

In some aspects, the transceiver further includes a decoder, a temperature sensor, and/or a humidity sensor.

Further provided herein are devices for detecting and transmitting a heat mount in a female animal. An exemplary device comprises a radio transmitter, a pressure switch, an encoder, an accelerometer, a circuit board, an antenna, a battery, and a hermetically sealed housing. The device is reusable or disposable.

Aspects of the present invention also provide methods of using an estrus detection system.

Also provided herein are methods for identifying an animal in estrus. The method comprises the steps of:
(a) placing a reusable or disposable device comprising a radio transmitter, a pressure switch, an encoder, an accelerometer, a circuit board, an antenna, and a battery, in a hermetically sealed housing on the tailhead of the animal;
(b) exposing the animal to a mounting animal;
(c) sensing through the device a mount of the animal by the mounting animal and generating data related to sensing the mount;
(d) transmitting the mount data to a transceiver;
(e) sending the mount data from the transceiver through a cellular link to a central server;
(f) repeating steps (c) through (e) at least once;
(g) processing the mount data using software linked to the central server, wherein the software comprises predetermined parameters for making a determination of estrus; and
(h) accessing the software to determine whether the animal is in estrus.

Still further provided herein are methods of characterizing the estrus cycle of a particular breed or species of animal (domestic or wild). The method comprises the steps of:
(a) placing a transmitter device comprising a radio transmitter, a pressure switch, an encoder, an accelerometer, a circuit board, an antenna, and a battery, within a hermetically sealed housing on the tailhead of a female animal of the particular breed or species;
(b) exposing the animal to a mounting animal;
(c) sensing through the device a mount of the animal by the mounting animal and generating data related to sensing the mount;
(d) transmitting the mount data to a transceiver;
(e) sending the mount data from the transceiver through a cellular link to a central server;
(f) repeating steps (c) through (e) at least once;
(g) accessing the mount data using software linked to the central server;
(h) making a determination of whether the animal is in estrus based on the data; wherein steps (c) through (h) are repeated over about 2 weeks to about 2 years to characterize the estrus cycle; and
(i) correlating the determination of estrus to the breed or species of animal and thereby characterizing the estrus cycle of the breed or species.

These and various features and advantages of the invention will be apparent from a reading of the following detailed description and a review of the appended claims.

BRIEF DESCRIPTION OF THE VIEWS OF THE DRAWINGS

FIG. 12 shows an exemplary transceiver set-up in accordance with an embodiment of the present invention.

FIG. 14 shows an illustrative main screen with several docked windows in accordance with one embodiment of the present invention.

FIG. 15 demonstrates how a transmitter set-up might appear in one embodiment of the present invention.

FIG. 16 demonstrates an exemplary report generated by the system software in accordance with one embodiment of the present invention.

DETAILED DESCRIPTION

Figure 1:
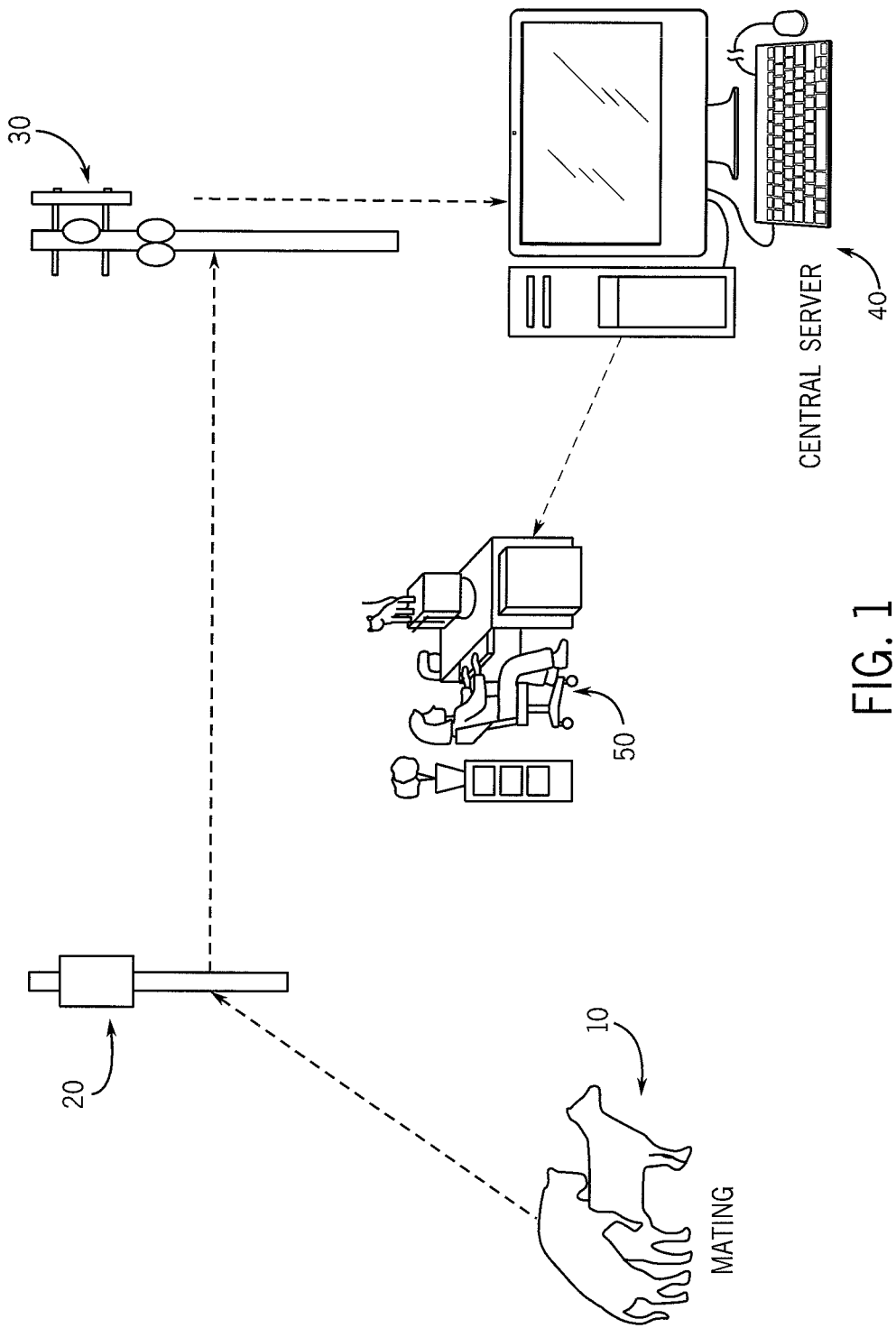
FIG. 1 is a flow diagram of an exemplary estrus detection system in accordance with one embodiment of the present invention.

Representative embodiments are provided below. While the invention will be described in conjunction with such embodiments, it will be understood that the invention is not intended to be limited to those embodiments. On the contrary, the invention is intended to cover all alternatives, modifications, and equivalents that may be included within the scope of the disclosure and any appended claims.

One skilled in the art will recognize many methods and materials similar or equivalent to those described herein can be used in and are within the scope of the practice of the present disclosure.

Unless described otherwise, technical and scientific terms used herein have the same meaning as commonly understood by one of ordinary skill in the art to which this disclosure belongs.

As used herein, the singular forms "a", "an", and "the" include plural references, unless the content clearly dictates otherwise, and are used interchangeably with "at least one" and "one or more". Thus, a reference to "repeater" includes one or more repeaters.

As used herein, the term "about" represents an insignificant modification or variation of the numerical value such that the basic function of the item to which the numerical value relates is unchanged.

As used herein, the terms "comprises", "comprising", "includes", "including", "contains", "containing", and any variations thereof, are intended to cover a non-exclusive inclusion, such that a system, device, process, method, etc.

that comprises, includes, or contains an element or list of elements does not include only those elements but may include other elements not expressly listed or inherent to such system, device, process, method, etc.

The phrase "estrous cycle" denotes the recurring physiologic changes induced by reproductive hormones in most mammalian placental females. Estrous cycles begin after puberty in sexually mature females and typically continue until death. The words "estrus" and "heat" refer to the phase of the estrous cycle when the female animal is sexually receptive ("in heat" or "on heat"). Gonadotropic hormones cause ovarian follicles to mature and increase secretions of estrogen. The female animal exhibits any number of sexually receptive behaviors including heat mounts. Typically, peak estrus immediately precedes ovulation and ovulation occurs spontaneously.

The phrase "heat mount" refers to an act in which an animal in heat is mounted by another animal. For example, in a group of 15 or 20 cows, an observer might notice a cow being mounted by another cow. If the mounted cow stands firmly when being mounted by the mounting cow, the mounted cow is likely in heat and the mount event is considered a "heat mount". However, if the mounted cow tries to move away from the mounting animal, the mounted cow is probably not in heat, thus no heat mount has occurred. A typical heat mount may last only 3 to 10 seconds.

The term "data" as used herein is inclusive of any information generated by the user including but not limited to animal identification numbers or transmitter identification numbers, any information generated by the transmitter including but not limited to status reports, mount data, duration, time of day, ambient temperature, humidity, and accelerometer measurements, and any information generated by the transceiver including but not limited to time of day, number of heat mounts, ambient temperature, and humidity. The term "signal" as used herein denotes data sent between the various components of system embodiments herein.

It is contemplated herein that the mounting animal can be any female animal of the same herd or can be a detector animal (teaser animal or gomer). An exemplary detector animal is a gomer animal (for example, a gomer bull, gomer billy, gomer ram, etc.) altered by vasectomy and/or penile deviation to prevent successful breeding without performing castration. Other detector animals such as androgenized females, for example, androgenized cows, heifers (freemartins), and emasculated animals (for example, steers, wethers, barrow, ox, etc.) can also be used to help producers detect estrus and are generally easier to handle than a gomer animal. Thus, one aspect contemplated herein is the use of a detector animal in combination with the methods and systems as described. Detector animals are available for all types of animals for which these methods, devices, and systems are useful. The term "mounting animal" is used herein to describe an animal that will mount an animal in estrus when given the opportunity to do so. As such, a "mounting animal" includes this same animal even when no mount occurs. In other words, a "mounting animal" is still a "mounting animal" whether a mounting event occurs or not.

Methods and systems described herein are useful in detecting estrus in a variety of animals, including for example, domestic animals, semi-domestic animals, captive wild animals, or wild animals. Illustratively, it is contemplated that the methods and systems described herein are applicable to estrus detection in females of the following animals: cattle (including *Bos taurus* and *Bos indicus*), goats, sheep, musk ox, reindeer, donkeys, horses, pigs, llamas, alpacas, yak, buffalo, bison, camels, deer, elk, water buffalo, etc. Breeding programs for domestic animals, semi-domestic animals, captive wild animals, and wild animals, as well as endangered species recovery programs can use the methods, devices, and systems described herein to identify the window of optimal breeding time, i.e. estrus. As used herein, "animal" or "female animal" or "mounted animal" are often used interchangeably and in general refer to a female animal in which a caretaker is interested in identifying a heat mount, onset of estrus, peak estrus, etc.

The phrase "peak estrus" refers to the optimal breeding time, often indicated by the time of peak mounting activity. Peak estrus can be determined by identifying the onset of estrus, some number of mounts in a specified period of time, for example, 3 or 4 mounts within a 3 or 4 hour time period, then plotting the distribution of heat mounts over time. As mounting activity increases, including duration and frequency, the probability that the animal is in estrus increases.

Existing methods of estrus detection are subject to a high number of false positives, for example, when an animal triggers an estrus detection device by bumping the detector against an object (a fence post, pole, tree, another resting animal, etc.), or when an animal upon being mounted tries to run away from the mounting animal. An observer of an instance described in the second example would know that the mounted animal was not in heat as she did not stand still (no "standing heat" or "standing mount"), however conventional heat detector technologies would not distinguish between a true heat mount and a mount that triggered the detector but was not a true mount, i.e., cows that move forward and pull away during mount are not in estrus. Existing detecting methods have unsuccessfully tried to exclude false positives by attempting to demonstrate a correlation between mount duration and veracity of the mount, however, the correlation is tenuous at best. Other detection methods can include combining several methods of identifying heat to minimize false positives. For example, a report generated at the University of Arkansas, Division of Agriculture, mentions minimizing false positives by combining chalk marking with a mount detector. See Table 1. Pennington, Heat Detection in Dairy Cattle, Printed by the University of Arkansas Cooperative Extension Service Printing Services. Chalk marking involves marking the tailhead of each female animal daily with chalk or crayon, then determining whether an animal has been mounted by looking at how much color has been rubbed off the animal by the mounting animal.

TABLE 1

Accuracy and Efficiency of Heat Detection During Continuous Observations for Cows with More than One Mount

| | Heat Detection Methods | | | |
| --- | --- | --- | --- | --- |
| Determinations | Three 30-minute visual observations per 24 hours | Mount detector | Chalk | Mount detector plus chalk |
| Percent efficiency in detecting estrus | 60.6 | 93.9 | 93.9 | 93.9 |
| Number of false positives | 0 | 28 | 38 | 3 |
| Percent accuracy of detection | 100 | 52.5 | 44.9 | 91.7 |

However, use of multiple methods of identifying heat increases costs in supplies and labor, cutting into already thin profit margins. For example, marking and inspecting each animal in a herd with chalk is costly, and the ability to confidently identify estrus is not easy during any 4, 6, 8, or 10 hour period, the period in which detection is critical.

Provided herein are systems, devices, and methods for detecting heat mounts in an animal, as well as systems and methods for determining estrus in an animal. Systems and methods described herein include the use of a device attached to the tailhead of an animal. The device includes a pressure switch which is activated in response to a mounting event, i.e., a second animal mounting the first animal where the device is attached to the tailhead of the first animal.

Provided herein are systems for detecting heat mounts in female animals to identify estrus and minimize false positive determinations. Such systems contain a device that includes a transmitter (attached to the tailhead of an animal), a transceiver, and a central server. FIG. 1 shows an illustrative system 5 in accordance with one embodiment of the invention. A transmitter 10 in a device of the invention is attached to the mounted cow 15 and sends a signal with the mount data to a transceiver 20 which relays the signal to a main receiving tower 30. From the main receiving tower 30 the signal is transferred to a central server 40. The end user 50 receives the data through a computer or a mobile device 55.

As used herein, "detecting" or "determining" or "identifying" with respect to an animal in heat or in estrus includes both the instruments required to observe and record a signal corresponding to a heat mount and the data output received by the user indicating onset of estrus or occurrence of a heat mount.

Figure 2:
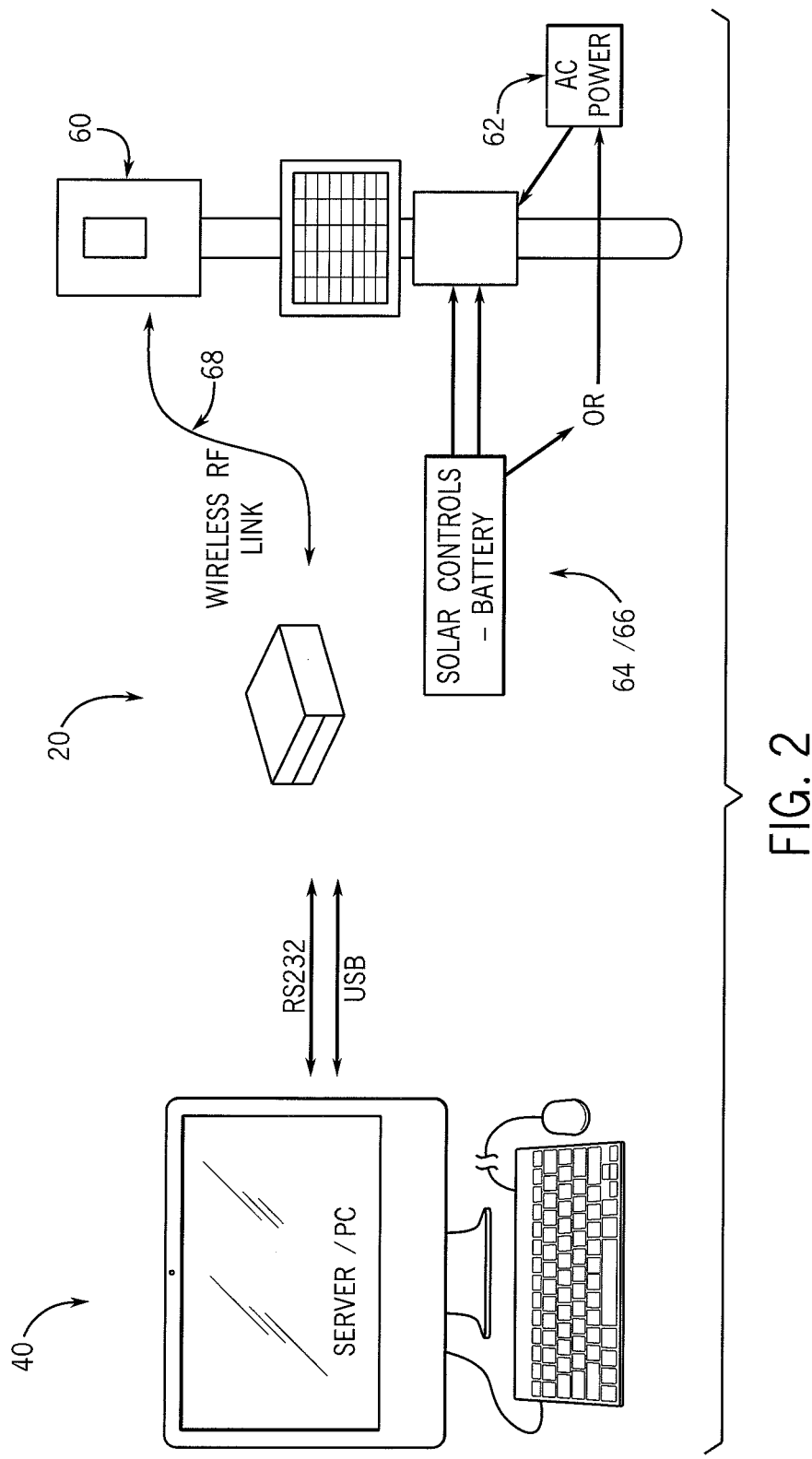
FIG. 2 demonstrates the use of a repeater with an estrus detection system in accordance with one embodiment of the present invention.

In some embodiments, a system 6 also contains one or more repeaters. FIG. 2 illustrates a system with a repeater 60, a transceiver 20, and a central server 40. The repeater 60 recognizes incoming data from a transmitter. A wireless RF link 68 carries the signal containing the data between the repeater 60 and the transceiver 20. The repeater can be powered by AC 62, by battery 64, and/or by solar controls 66 (with or without a battery for energy storage). An example of such unit is shown in FIGS. 17 and 18.

Data received by the transceiver can be repackaged and sent to the central server by cellular link, a Radio Frequency (RF) link, a Wi-Fi wireless link, or a combination of such links. Other conventional methods of data transfer may be used including, for example, IR, USB, RS-232, etc., to a PC, which then uploads the data to the central server. RS-232 (Recommended Standard 232) is a standard for serial binary data signals connecting a DTE (Data Terminal Equipment) and a DCE (Data Circuit-terminating Equipment) and is commonly used in computer serial ports. A similar ITU-T standard is V.24.

Figure 3:
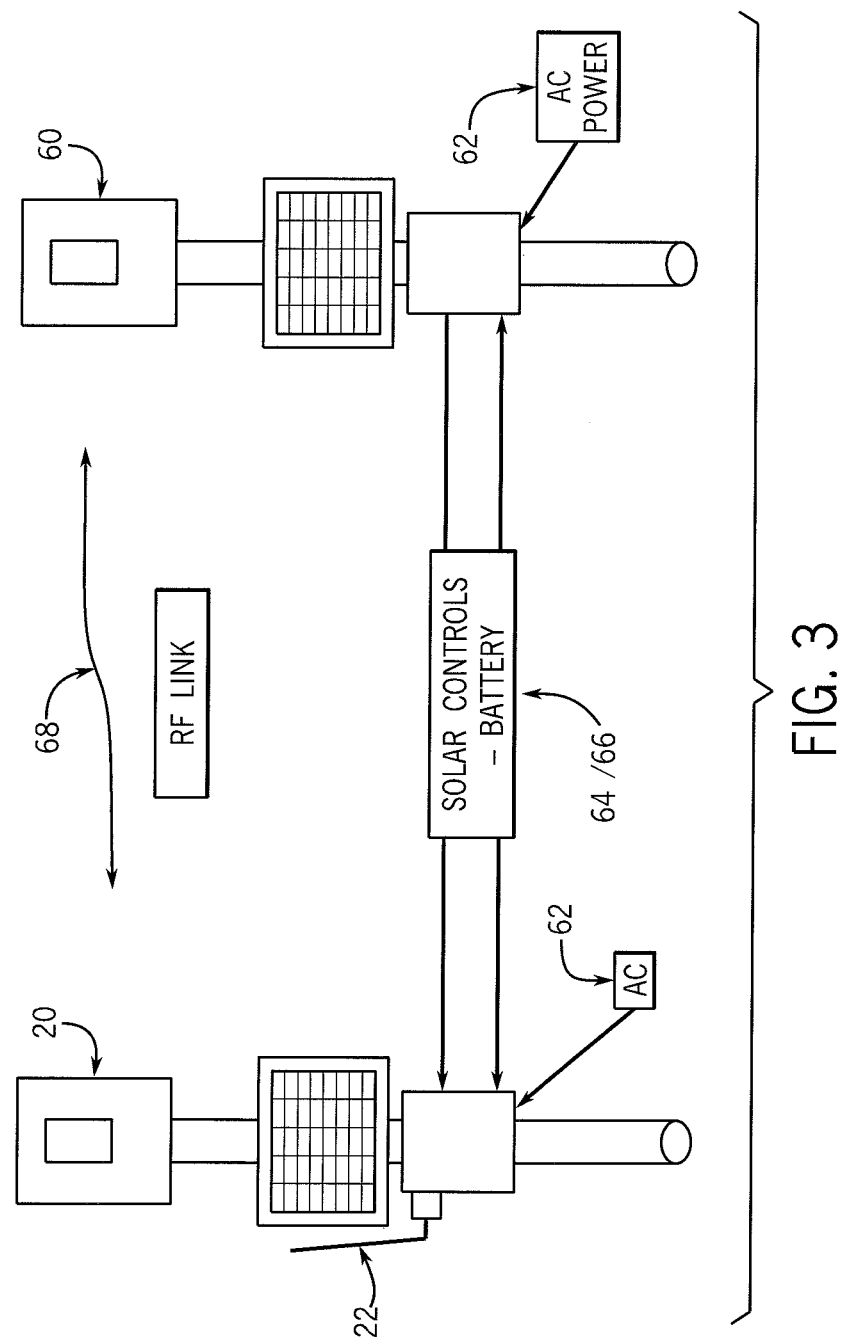
FIG. 3 demonstrates the use of a repeater and a cellular transceiver with an estrus detection system in accordance with one embodiment of the present invention.

FIG. 3 is an illustrative embodiment of a system 7 showing a repeater 60 and a cellular transceiver 20. The repeater 60 receives a signal from a transmitter of the invention and using RF, retransmits the signal to a cellular linked transceiver 20. The transceiver 20 has an antenna 22 and can be battery powered, AC powered, and/or solar powered. The antenna 22 is preferably a dual antenna array including an omni directional antenna component for receiving RF mounting signals from the transmitter 80. Data is preferably stored in a "buffer" in the transceiver 20 until such time as the user decides to review the data. Data is sent to the computer utilizing a unidirectional antennae component. The main receiving tower 30 has a similar unidirectional antenna. The omnidirectional antennae is preferably a 900 MHz device (up to 6 dbi). The unidirectional antennae of preferably a 2.4 GHz (up to 10 dbi). The 900 MHz antenna permits transmission of data from the transmitter 80 on the cow to the transceiver 20 over large distances. The 2.4 GHz antennae permits transmission of accumulated data from the transceiver to the server 40 at high data transfer speeds. The repeaters 60 send and receive data preferably by way of twin 900 MHz antennas.

Figure 17:
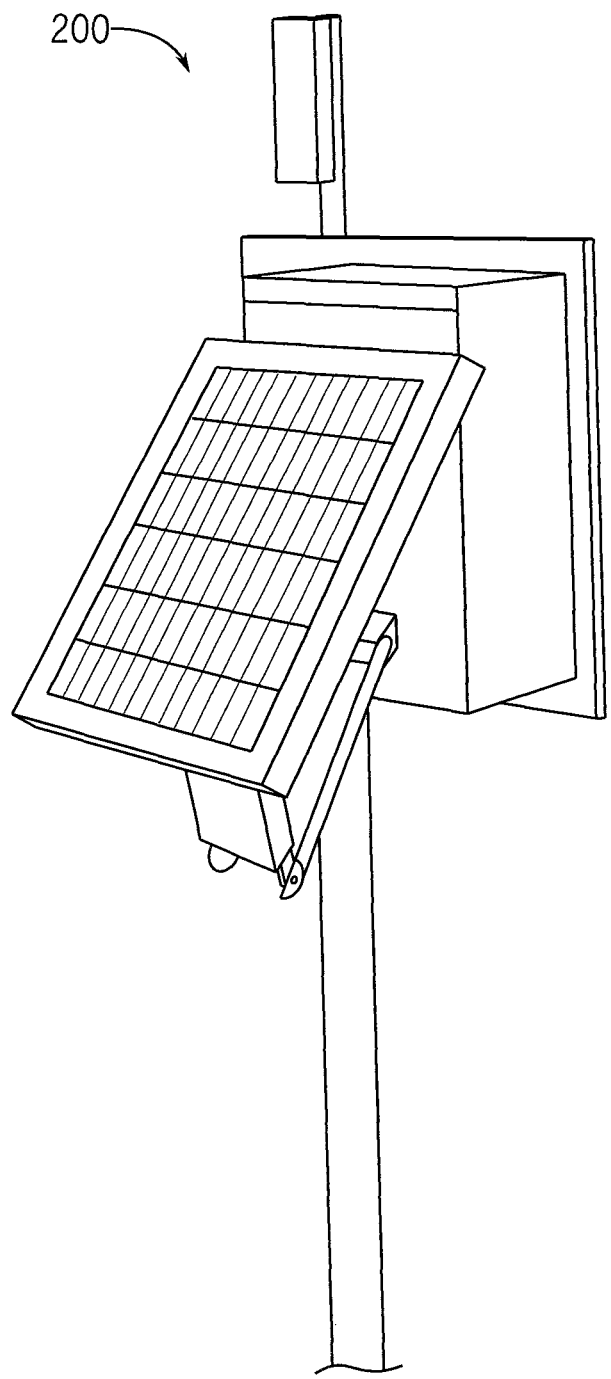
FIG. 17 shows an embodiment of a solar powered unit of the present invention.
Figure 18:
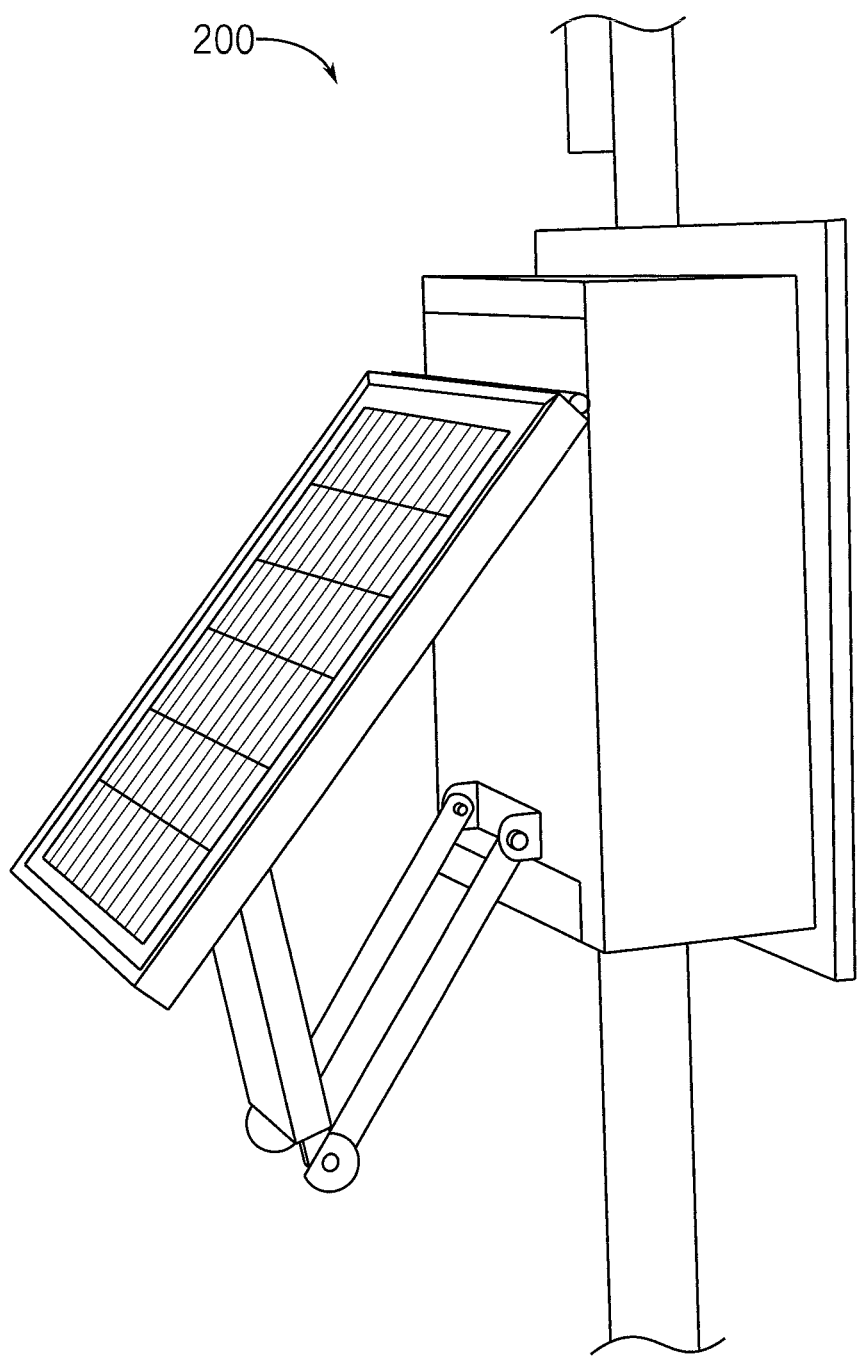
FIG. 18 shows a detailed view of the solar powered unit.

FIGS. 17 and 18 show a further embodiment of the transceiver 200.

RF or Wi-Fi Wireless links may be used with or in place of the cellular links.

In either of the embodiments shown in FIGS. 2 and 3, the repeater 60 retransmits data received from the transmitter over or around a large object to another repeater or to the transceiver 20.

Figure 4:
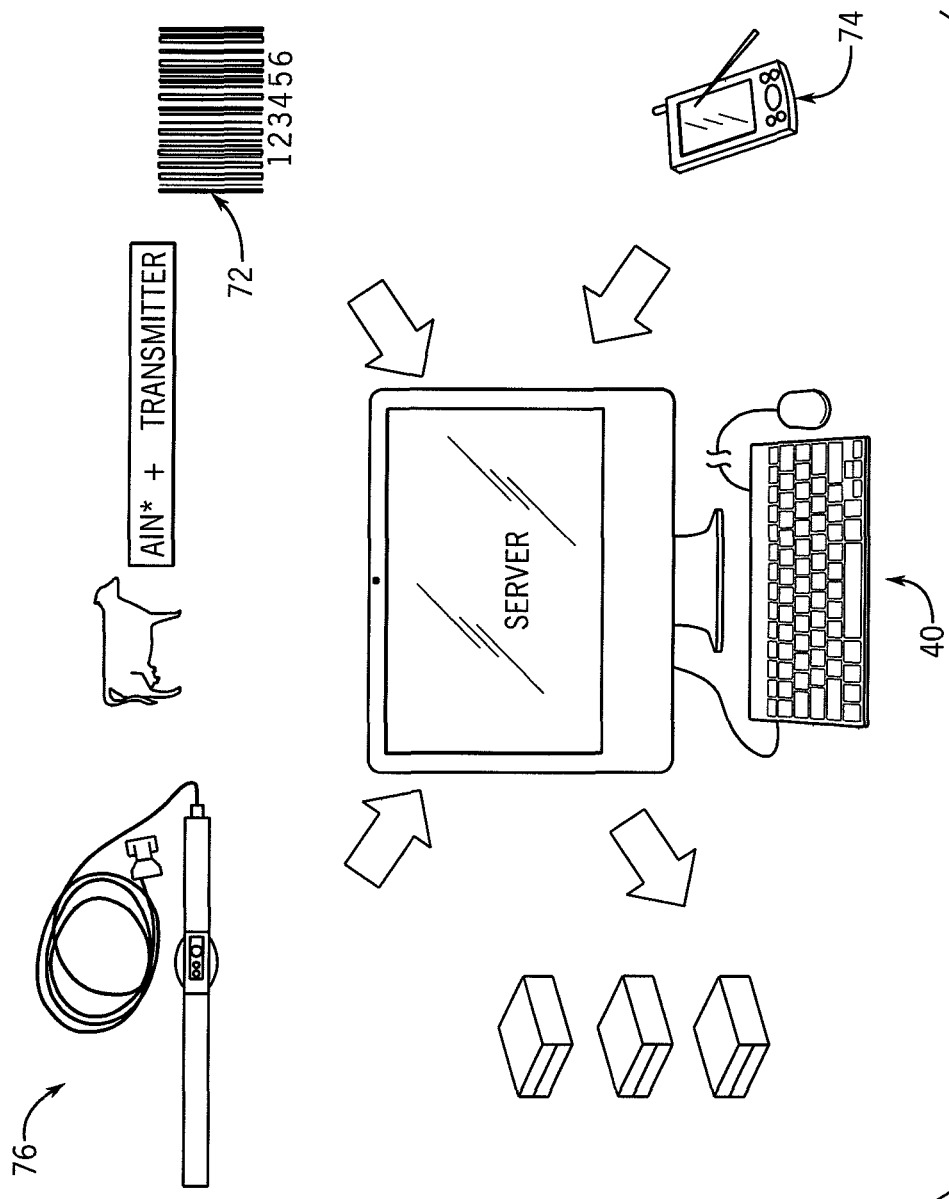
FIG. 4 illustrates exemplary devices for entering data into a system in accordance with one embodiment of the invention.

In some embodiments, the system also contains one or more data entry devices. FIG. 4 illustrates various methods and devices for entering data including animal identification numbers and/or transmitter identification numbers into the database on the central server 40. In some embodiments, a transmitter identification number is assigned to the animal's identification number. Barcode readers 70 can read barcodes 72 on transmitters and wands 76 can recognize animal identification numbers on ear tags or implanted chips. Such data is uploaded to the server 40 directly or through the use of IR, flash cards, memory chips, USB ports, etc. Likewise, animal identification numbers and/or transmitter identification numbers can be entered into a PDA (personal digital assistant) 74, cell phone, and/or laptop and communicated to the central server. Compatibility with various types of data entry devices allows the user greater flexibility when entering data in the field.

Descriptions of the elements of the system are provided only for an understanding of the various embodiments. One skilled in the art will appreciate that the methods, devices, and systems described herein can be implemented without using all of the elements or without using the specifically mentioned elements.

Surprisingly, the systems and methods described herein provide a practical and effective way to determine and exclude false positives. For example, in one embodiment, an accelerometer provides an electromechanical method of measuring acceleration forces such as forward movement or tilt relative to earth's gravity. Thus, data indicating forward momentum or tilt at the time a mount occurs can be used to verify whether a "true mount" has occurred. In some embodiments, data generated by the accelerometer is sent by the transmitter along with data indicating a mount occurred. In other embodiments, data indicating occurrence of a mount will be prohibited when the accelerometer indicates forward momentum or tilt. In either event, the mount data can be excluded as a false positive.

Thus, provided herein are systems for determining estrus in an animal or systems for identifying an animal in estrus. In some embodiments, the system comprises (a) a detection device comprising a hermetically sealed transmitter housing enclosing a radio transmitter, a pressure switch, an encoder, an accelerometer, a circuit board, an antenna, and a battery. The housing and its contents are reusable or disposable. In some aspects, the housing is attached to a stabilization device. The system further comprises (b) a transceiver comprising a tuner, a power source, an antenna, and a cellular link and (c) a central server. The system can further comprise one or more repeaters and/or one or more data entry devices. The detection device can further comprise a GPS receiver and/or a counter. The transceiver can further comprise a decoder.

In some embodiments, the system comprises (b) an RF link rather than a cellular link or an RF link in combination with a cellular link.

The central server (c) can comprise software from which a user can access data compiled by the server. The central server and/or software can access data from a cellular transmission, a website, other software, another server, another computer, through USB, and/or through IR.

Also provided herein are methods for identifying an animal in estrus. The method comprises the steps of:

(a) placing a transmitter device comprising a radio transmitter, a pressure switch, an encoder, an accelerometer, a circuit board, an antenna, a battery, in a hermetically sealed housing on the tailhead of the animal;
(b) exposing the animal to a mounting animal;
(c) sensing through the device a mount of the animal by the mounting animal and generating data related to sensing the mount;
(d) transmitting the mount data to a transceiver;
(e) sending the mount data from the transceiver through a cellular link to a central server;
(f) repeating steps (c) through (e) at least once;
(g) processing the mount data using software linked to the central server, wherein the software comprises predetermined parameters for making a determination of estrus; and
(h) accessing the software to determine whether the animal is in estrus.

In alternative embodiments, the sensing through the device includes verification of a standing mount by analysis of false positive data.

The predetermined parameters can include, for example, at least three mounts in a three hour period or at least three mounts in a four hour period. In some embodiments, estrus is determined to begin at the first of the at least three mounts in a specified time period.

In most embodiments, the user can access the software through a computer, PDA, cell phone, etc.

In some embodiments, systems and devices described herein are useful in characterizing the estrus cycle of a particular breed or species. For example, the estrus cycle of an endangered species involved in a captive breeding program may be unknown or poorly characterized. The estrus detection system can be used to identify the number of days between an estrus cycle, the length of an estrus cycle, and/or how a female animal of that breed or species exhibits estrus (i.e. how many standing mounts within a particular time frame indicate estrus). Such information would be useful not only for the breeding program, but also for science in general.

Thus, further provided herein are methods of characterizing the estrus cycle of a particular breed or species. The method comprises the steps of:

(a) placing a transmitter device comprising a radio transmitter, a pressure switch, an encoder, an accelerometer, a circuit board, an antenna, and a battery, within a hermetically sealed housing on the tailhead of a female animal of the particular breed or species;
(b) exposing the animal to a mounting animal;
(c) sensing through the device a mount of the animal by the mounting animal and generating data related to sensing the mount (in some embodiments this includes an analysis and/or tabulation of tilt, movement, etc. that indicates a standing mount);
(d) transmitting the mount data to a transceiver;
(e) sending the mount data from the transceiver through a cellular link to a central server;
(f) repeating steps (c) through (e) at least once;
(g) accessing the mount data using software linked to the central server; and
(h) making a determination of whether the animal is in estrus based on the data;

wherein steps (c) through (h) are repeated over about 2 weeks to about 2 years to characterize the estrus cycle.

Additional parameters can be assessed including, humidity, temperature, etc., where such parameters can be statistically analyzed for correlative connections to estrus.

Detection Device

A transmitter is an electronic device that generates and propagates an electronic signal. As used herein, a transmitter uses radio frequency (RF) data communication technology to transmit mounting data including, for example, an animal identification number and/or a transmitter identification number to a transceiver.

Figure 5:
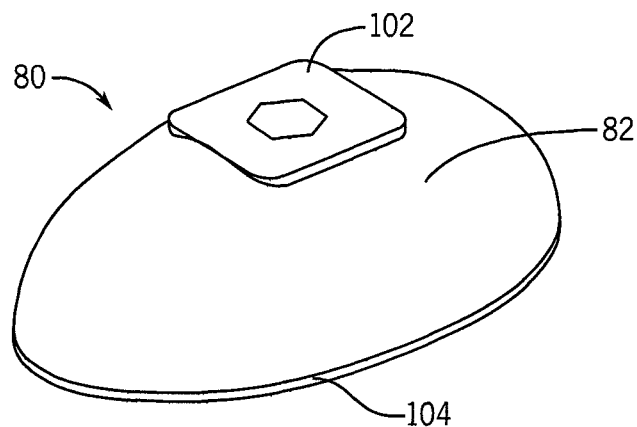
FIG. 5 is a perspective view of one embodiment of the transmitter assembly in accordance with the present invention.

An external view of a transmitter 80 in accordance with one embodiment described herein is shown in FIG. 5. The transmitter is contained in a housing 82 and the housing 82 is hermetically sealed, in this embodiment, by an ultrasonic welded seal 104. Other means of hermetically sealing the housing are contemplated herein, including, for example, brazing, welding, metalizing, etc. A pressure switch cover 102 provides a place in the housing 82 for the pressure switch to come into contact with a mounting animal. Generally, the pressure switch extends upwardly away from the cover 102 to present a compressible contact for mount detection.

In one embodiment, the transmitter device contains an RF printed circuit board, a pressure switch, an antenna, and a battery. The battery is held in place, for example, by soldering, to prevent the battery from moving around in the housing and potentially damaging other transmitter components. The transmitter is hermetically sealed in a rigid or semi-rigid material, for example, a hardened plastic housing.

In some embodiments, the detection device further contains an accelerometer and/or a GPS receiver.

Figure 6A:
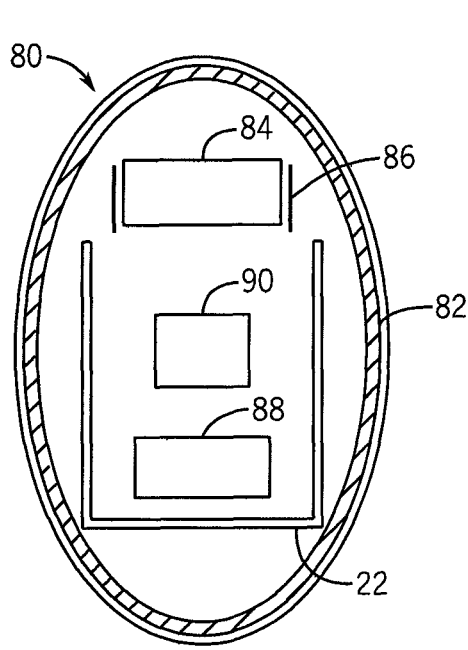
FIGS. 6A-C are views of the inside of a transmitter, a side view of a pressure switch assembly, and an exploded view of a pressure switch assembly, each in accordance with an embodiment of the present invention.

In more detail and referring to FIG. 6A, a detection device embodiment is shown within a housing 82 and encases a transmitter 80, a pressure switch assembly 90, a battery 84 held in place by permanently soldered battery clips 86, and an antenna 22. In this embodiment, an accelerometer 88 is also provided. The battery 84 is preferably rechargeable so that the transmitter 80 is reusable. Rechargeable batteries permit use for about 3 months and up to approximately 500 recharges.

Transmitter embodiments herein can be programmed with a transmitter identification number. This number is typically sent as outgoing data to a transceiver embodiment. The transmitter can alternatively or also be programmed with the identification number of an animal of interest. This number can also be sent as outgoing data to the transceiver. Typically, either or both identification numbers are packaged with outgoing heat mount data.

Figure 7:
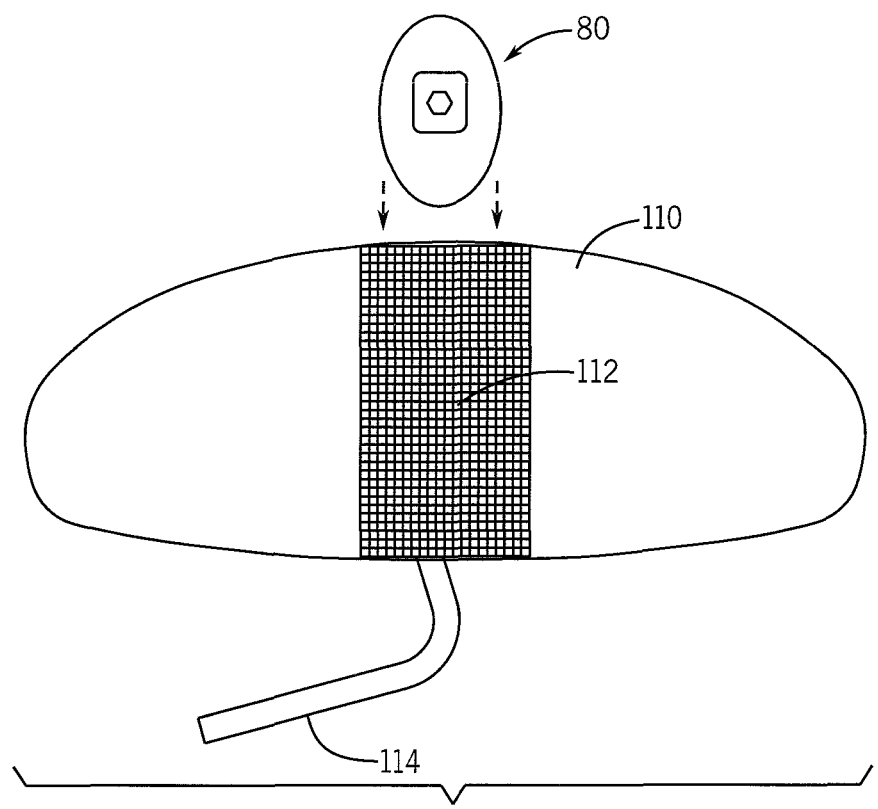
FIG. 7 is a top view of a transmitter and a patch assembly in accordance with one embodiment of the present invention.
Figure 8:
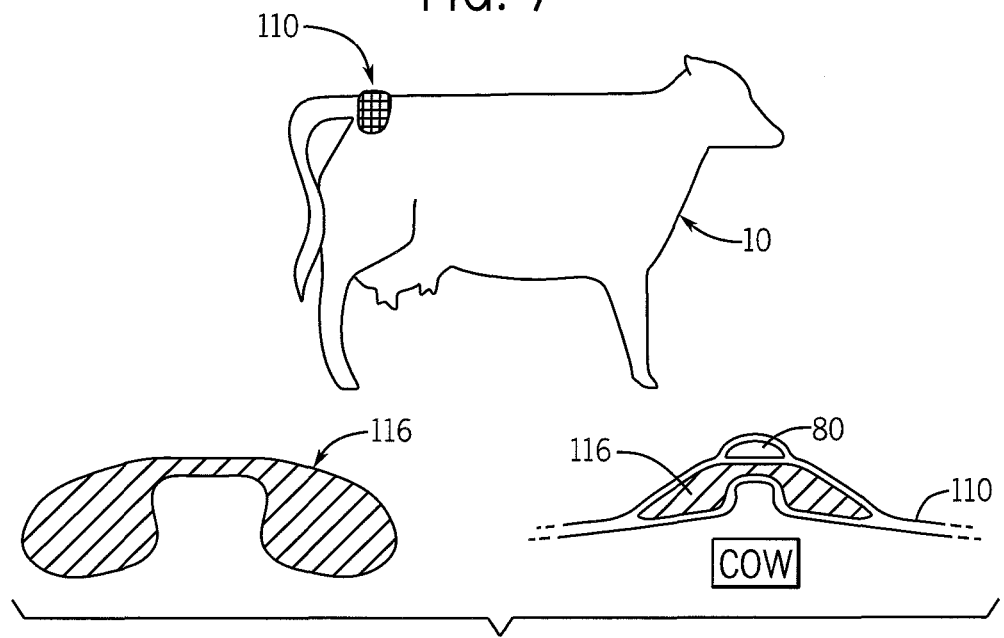
FIG. 8 is a drawing of a transmitter within a patch attached to an animal. An optional stabilization device is also shown.

In some aspects, the detection device is inserted into a patch which is ergonomically designed to fit the contour of an animal's tailhead, for example, the tailhead of a cow (see FIGS. 7 and 8, for example). The shapes and pronouncement of animals' tailheads vary significantly. Some tailheads are very flat, others are very steep and sharp, and others fall somewhere in between. The patch can be shaped to fit the tailhead of each animal such that there is no empty space between the transmitter and the surface of the animal's skin. Shaping of the patch helps eliminate rocking of the transmitter during mounting activity. Referring to FIG. 7, the detection device is inserted into a patch 110. In this embodiment, the patch 110 is made of polyester mesh, however, any useful material is contemplated herein. The patch 110 contains a transmitter compartment 112 in which the transmitter 80 is inserted. In some embodiments, a safety strap 114 is attached to the patch 110 to facilitate easy removal of the patch from the animal.

In an alternative aspect (or in addition to the aspect described above), the detection device can be stabilized using a "stabilization device". An exemplary "stabilization device"

is constructed out of thin vinyl-like material and includes at least two compartments which fit beneath the transmitter. The compartments can be filled with any material which provides stability, including, for example, sand, rice, etc. The compartments fill empty space between the outer part of the bottom of the transmitter and the sides of the tailhead. Any shape or size of the stabilization device is contemplated herein, as long as it functions to substantially prevent or eliminate rocking of the transmitter during mounting activity. As used herein, the word "substantially" indicates that some rocking can still occur but not to the extent that it would without the stabilization device. FIG. 8 illustrates the placement of the patch 110 on the tailhead of an animal, in this instance a cow 10. A stabilization device 116 is placed beneath the patch 110 containing the transmitter 80. As can be seen from the Figure, the stabilization device 116 provides a more level surface for placement of the transmitter 80.

In some embodiments, the detection device is disposable—for this embodiment, the battery cannot be exchanged without destroying the case and breaking the hermetic seal. The hermetic seal prevents moisture and dirt from entering the housing, thus extending the usable life of the transmitter to the life of the battery. A typical battery such as a lithium iodide battery has an average life of 3½ years, though batteries with longer life spans are contemplated herein. The battery may alternatively be rechargeable and reusable.

As used herein, the term "disposable" refers to a transmitter designed for use in about 1 to 4 breeding seasons, for example, about 2 or about 3 breeding seasons. In other words, the transmitter does not last indefinitely.

Use of a disposable, hermetically sealed detection device addresses any one or more of the following problems and provides an unexpected benefit to the user: (1) the circuit board is protected from damage caused by moisture and dirt seeping through screw holes and gaskets, conditions that least to an enhanced rate of failure for the device; (2) damage to the circuit board caused by static from opening the housing to change the battery is eliminated; (3) eliminating the need to change the battery eliminates breakage of the battery clips within the transmitter housing; and (4) batteries are dangerous to curious animals and a hermetically sealed housing reduces the likelihood that an animal might come into contact with a battery separated from the transmitter.

In some embodiments, the transmitter is mounted to the sacrum (tail head) of the animal using glue or similar adhesive. The glue can be attached to an adhesive strip, while the adhesive strip is in turn attached to the transmitter. It is contemplated herein that some or the entire bottom portion of the transmitter housing is made of a material receptive to an adhesive (or adhesive strip) while the upper portion of the housing can be made of the same material or a different material with smoother characteristics. See FIG. 8 illustrating attachment of a transmitter to the tailhead of an animal such as a cow.

In other embodiments, the detection device is inserted into a patch and the patch is mounted to the tail head of the animal. As above, the patch can be mounted to the animal using glue or similar adhesive, an adhesive strip, etc. Some or the entire bottom portion of the patch can be made of a material receptive to an adhesive (or adhesive strip) while the upper portion of the housing can be made of the same material or a different material with smoother characteristics.

In still other embodiments, a detection device herein is inserted into a patch and the patch is adhered to a stabilization device. The stabilization device is attached to the tail head of the animal using glue or similar adhesive, an adhesive strip, etc. Some or the entire bottom portion of the stabilization device can be made of a material receptive to an adhesive (or adhesive strip). The patch can be permanently or temporarily attached to the stabilization device using adhesive, screws, clamps, etc.

In use, pressure from the brisket of the mounting animal activates the pressure switch causing the transmitter to send the transmitter identification number (with or without additional data) to the repeater or transceiver. In some embodiments, the transmitter sends the data immediately upon activation of the pressure switch. In other embodiments, the transmitter sends the data after a threshold duration, for example, after 1 second, after 2 seconds, after 3 seconds, after 4 seconds, or after 5 seconds, etc. from the time the mount begins. In still other embodiments, the transmitter sends the data upon release of the pressure switch, i.e. when the mount is finished.

A threshold amount of pressure required to activate the pressure switch can be set according to the type of animal in which the detector is being used. For example, in cattle, elk, and deer, the threshold pressure can be about 50 pounds, in sheep and goats, about 5 to 10 pounds, etc. One skilled in the art is capable of making a determination of threshold pressure appropriate for the type of animal. Thus, for example, if the pressure switch is ⅛ of an inch above the surface of the transmitter housing, it would take a mounting cow to apply 50 pounds of pressure to the pressure switch to compress the pressure switch ⅛ of an inch.

Figure 6B:
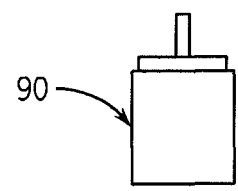
Figure 6C:
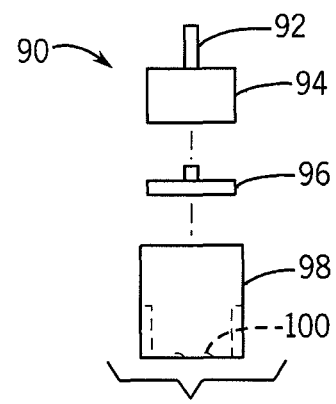

Activation of the pressure switch occurs outside the housing by the action of the brisket of the mounting animal placing pressure on the switch. Inside the housing, the circuit board includes, along with the necessary circuitry, several switch contacts. FIG. 6B shows a side view of a pressure switch assembly 90. FIG. 6C shows the various components of a pressure switch assembly 90 in accordance with one embodiment herein. A switch disk 94 physically and electrically connects the upper 96 and lower 100 contacts within the housing 98 when the pressure switch 92 (on the outside of the transmitter) is pressed or activated. The pressure switch 92 is connected to the switch disk 94. Connection of the upper 96 and lower 100 contacts upon activation of the pressure switch 92 activates the transmitter 80 to generate mounting data.

After completion of a mount event, a timer circuit directs the input of data into an encoder that packages the data with a carrier signal. A conventional RF transmitter then sends the encoded data at a predetermined frequency to a repeater or transceiver. Data can be sent any predetermined number of times per mount, for example, the data can be sent once, twice, three times, four times, five times, six times, seven times, etc.

Duration of the mount is measured using a counter. In some embodiments, mount data is sent from the transmitter after a mount that lasted for some threshold period of time. For example, the threshold can be at least about 3 seconds, at least about 4 seconds, or at least about 5 seconds. However, the duration time itself is not sent to a transceiver, just data indicating a mounting event has occurred (subject to other data as described below).

In response to activation of the pressure switch, the transmitter sends data to the repeater or transceiver. Such data can include but is not limited to transmitter identification number, animal identification number, accelerometer data, GPS data, duration of the mount time, time of day, date, and/or number of mounts in a predetermined time period. Additionally, the detection device can be equipped to measure and transmit air temperature data and/or relative humidity data at the time of the mount. The sensor can be mounted on the housing or within a port in the housing. The phrases "mount data", "mounting data", "heat mount data", etc. are used interchangeably herein and refer to any of the above data types as well as any combinations thereof.

Power on, standby, power from battery applied to circuitry, counters (for duration), error codes, etc. are provided.

In one embodiment, a jumper switch on the circuit board allows the transmitter to send data in the desired frequency. Frequencies can be changed and set to 902-928 MHz (North America), 868-870 MHz (Europe), 915-928 MHz (Australia), or 922-928 MHz (New Zealand). These frequency settings comply with worldwide RF regulations.

In some embodiments, the transmitter contains a supervisor or status function indicator which monitors the functionality of the transmitter. For example, each transmitter can send a status signal on a regular basis, e.g. every hour, every two hours, every three hours, every four hours, etc. If the transmitter's status signal fails to be received, a message such as a text message is sent by the transceiver to the central server or to the user's cell phone. Functionality includes, for example, information regarding battery power. If the battery power is low, the message could indicate in some aspects that the transmitter should be replaced.

In some embodiments, a code on a transmitter chip instructs the transmitter to go through perpetual sleep/wake cycles.

In some aspects, as discussed above, the detection device contains an accelerometer. The accelerometer can be used to screen out false positives, e.g. mounts that are not standing mounts, where the mounted animal tries to move away from the mounting animal, or contact by the animal with an object such as a post or tree. In some embodiments, if the animal's motion forward is abnormal or if the accelerometer detects abnormal tilt during activation of the pressure switch, accelerometer data will be sent with the mount data; if no abnormal motions are detected, no accelerometer data will be sent. In other embodiments, accelerometer data is sent with every transmission of mount data. Accelerometer data is typically packaged with the mount data.

In some aspects, the detection device contains a GPS receiver. A GPS receiver allows a user to identify the location (including latitude, longitude, and altitude) of a transmitter whether still attached to the animal or lost in a pasture or corral.

Thus, provided herein is a device for detecting and transmitting data indicating a heat mount in a female animal. The device comprises a radio transmitter, a pressure switch, an encoder, an accelerometer, a circuit board, an antenna, a battery, and a hermetically sealed housing. The device can be disposable. In some embodiments, the device further comprises a GPS receiver, a counter, and/or a stabilization device. The pressure switch activates when the female animal is mounted by a mounting animal to generate mounting data. The accelerometer can generate data regarding motion of the animal and such data can be transmitted along with the mount data. In some embodiments, the accelerometer data indicates whether a standing mount has occurred.

Data Entry Device

The system can include a data entry device. This device, in some embodiments, is a portable, electric or battery powered device that uses RF to transmit data to the transceiver. Exemplary devices include a barcode scanner or wand. The transceiver then sends the data to a central server. Alternatively, the data entry device uploads the data directly to a computer, website, or a server database. The portable device can be used onsite as a user attaches each detection device to an animal and records the transmitter identification number with the animal identification number. In other embodiments, the data entry device is simply a laptop computer, personal computer, personal data assistant, cell phone, etc. where the data is entered directly into the software on the website. The identification numbers can be initially stored on the computer before uploading to the website, or if internet access or wireless access is available, the numbers can be directly entered into the server database.

High Power Repeaters

Large farms, dairies, ranches, or geographic areas containing animals being monitored often contain obstacles such as hills or buildings which block transmission of data from the transmitter to the transceiver. Likewise, large areas and long distances tend to dilute a transmission making data reception spotty and inaccurate. A repeater is an electronic device that receives data from the transmitter and retransmits the data at a higher level and/or higher power or onto the other side of an obstruction such that the data can be moved over longer distances. In the system described herein, one or more repeaters can be placed in an area near animals that might be a long distance away from the transceiver or on the away side of an obstacle. The repeater includes an RF receiver tuned to the frequency of the carrier signal of the transmitter. The repeater receives mount data from the transmitter and re-transmits at full power the RF messages to the transceiver. A repeater can effectively increase the range of transmission by up to about 4 miles in line-of-sight to the transceiver.

Figure 9:
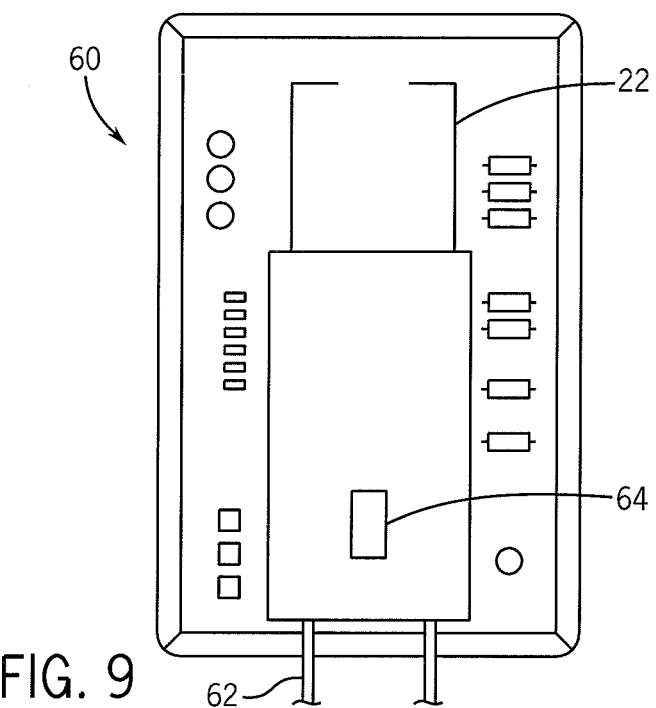
FIG. 9 is a schematic of a repeater in accordance with one embodiment of the present invention.

FIG. 9 shows a repeater 60 with an antenna 22 and a microprocessor 64. In this embodiment, the repeater 60 is electrically powered as wires 62 to power are shown exiting the repeater 60. The antenna 22 receives an RF signal emitted from a transmitter.

Transceiver

A transceiver is a device having both a transmitter and a receiver sharing a common circuitry or single housing. A transceiver also has an antenna. As used herein, the transceiver receives and sends mount data, including an animal identification number and/or a transmitter identification number. The transceiver can operate to receive data sent by RF and to send data either by RF or cellular transmission. The transceiver can use advanced RF technology with diversity reception and advanced signal processing to minimize nulls, or dead spots, and provide superior performance in noisy RF environments.

Figure 10:
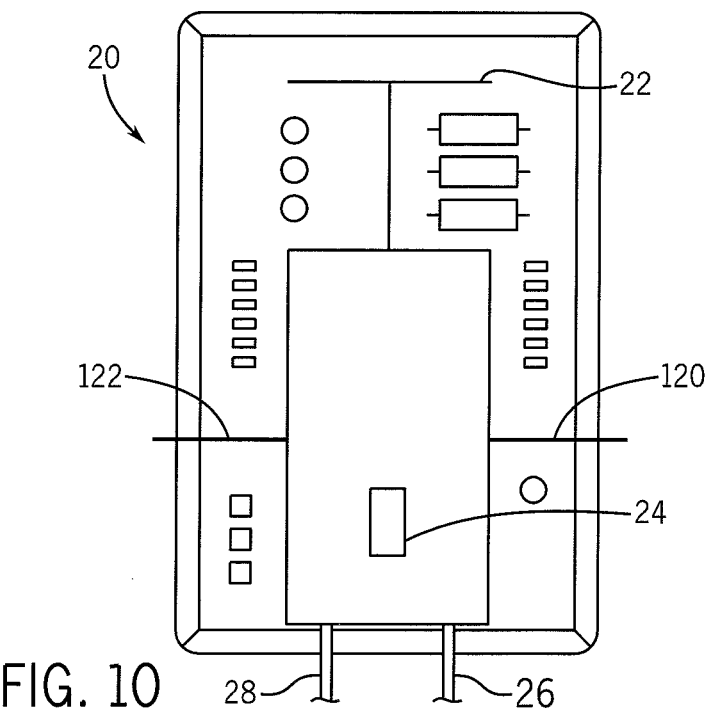
FIG. 10 is a schematic of a transceiver in accordance with one embodiment of the present invention.

FIG. 10 shows an illustrative transceiver 20 having an antenna 22 and a microprocessor 24. A microprocessor 24 is essentially an integrated circuit usually on a single chip that performs the bulk of the processing and controls the transceiver 20.

The transceiver can be encased in a weather-resistant enclosure. The transceiver can be powered by a conventional power source, by solar panel, and/or a battery. The transceiver can be powered by either an 110V outlet or 12V DC power. The transceiver can be placed 15 to 50 feet in the air in the proximity of the animals being monitored (though other appropriate heights are also contemplated including heights below 15 feet and heights above 50 feet). The distance between the animals being monitored and the transceiver is typically less than about ½ mile. If a greater distance between the animals and the transceiver is necessary, a repeater can be used as described above. The transceiver receives mounting data from the transmitter or repeater and sends the data to a central server. The central server monitors the power status of the transceiver. In some embodiments, should the cellular link go down, the user is notified through a text message for example, sent from the central server.

In some embodiments, when the transceiver sends mount data received from the transmitter, it also sends data recording the time of day the mount data was received. In other embodiments, the transceiver sends the number of mounts occurring in a predetermined time period for a particular animal.

Referring again to FIG. 10, in some embodiments, the transceiver also has a humidity sensor 122 and/or a temperature sensor 120. Thus, when the transceiver sends mount data, it can also send data recording ambient air temperature and/or humidity levels at the time the mount data was received. Flexible programming allows the user to include adjustable measurement and transmit interval times, or the option to transmit mount data occurring only within a particular temperature range and/or humidity range. In some aspects, humidity and/or temperature data is not necessarily sent with the mount data but is rather transmitted when a respective fluctuation in temperature or relative humidity occurs.

Exemplary temperature monitoring ranges include about −4° F. to about 140° F., or about 10° F. to about 140° F., or about 10° F. to about 120° F., or about 20° F. to about 120° F., etc., and any range falling within such ranges. The term "about" reflects a 0.1° F. to 5° F. temperature difference outside the stated range.

Exemplary humidity monitoring ranges include from about 0% to about 100% relative humidity, or about 0% to about 90% relative humidity, or about 5% to about 90% relative humidity, etc., and any range falling within such ranges. The term "about" reflects a 0.5% to 5% relative humidity difference outside the stated range.

In some embodiments, the humidity and/or temperature data is used to study their respective or combined effects on occurrence of estrus. In other embodiments, the humidity and/or temperature data is used to screen out false positives. In still other-embodiments, the humidity and/or temperature data is used to optimize a determination of estrus or peak estrus.

The transceiver receives data in RF and, in some embodiments, can transmit data to the central server in RF. RF is a frequency or rate of oscillation of electromagnetic radiation within a range of about 3 Hz to 300 GHz. In order to receive radio signals, a radio antenna and a radio tuner are used. The tuner identifies the particular frequency used by the transmitter. As mentioned above with respect to the transmitter, the frequency used by the transceiver can be set to operate within rules of any given country.

In some embodiments, the transceiver lacks a cellular link. In such instances, the transceiver can transmit data wirelessly using RF to an access point, up to about 25 miles, to a small box with an antenna. The box contains a memory chip integrated into a circuit board and the capacity to transfer data to a nearby computer, i.e. a laptop brought to the site by the user, using infrared (IR), a USB link, a flash card, etc.

In other embodiments, the transceiver transmits data using one or more cellular networks. A cellular network is a radio network made up of a number of radio cells each served by at least one fixed-location transceiver, a cell site or base station. Several major cellular carriers have made their vast cellular networks available to companies for widespread, inexpensive data transfer. Unlike a typical cell phone, the cell link can remain active continually and the carrier bills the user based on the amount of data sent and not on the number of minutes the link is active. For example, the user would be billed for any data sent to or received by the transceiver using cellular transmission.

Figure 11:
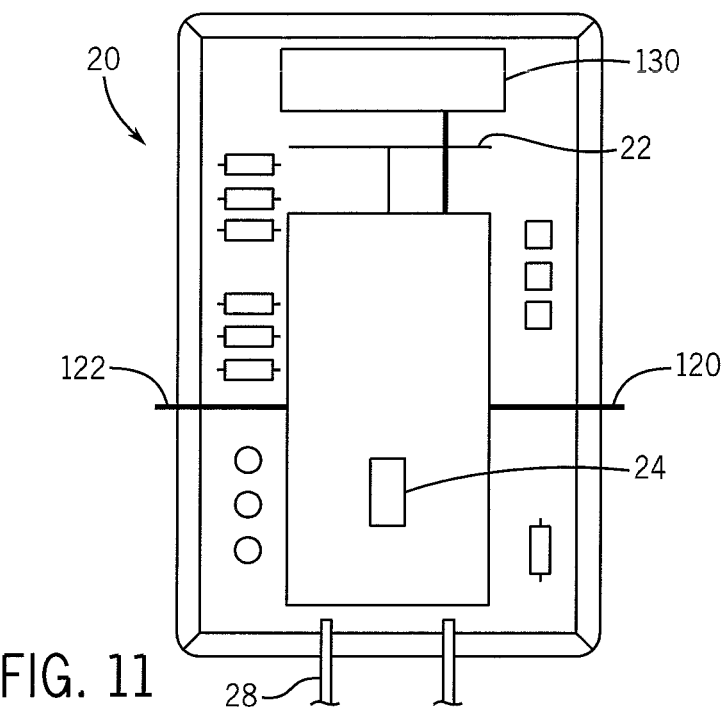
FIG. 11 is a schematic of a transceiver with cellular transmission capacity in accordance with one embodiment of the present invention.

Cellular networks have increased capacity over RF, reduced power usage, cover a larger area, and pick up reduced interference from other signals. FIG. 11 is an illustrative embodiment showing an RF/cellular transceiver 20. Such a transceiver 20 can have both a cellular transmitting element 130 and an antenna 22. The antenna 22 receives a signal from a transmitter or repeater. The cellular transmitting element 130 sends the data to the central server via a cellular network.

Central Server

The user can access the data from any computer with internet access. For example, the user can access a predetermined website, can enter the user account name, can enter the password corresponding to the user account, and is logged onto the site where the software displays the data specific for that user.

Access to the data on the internet addresses a long-felt need. Typically, software for available methods of estrus detection is run on the local computer. Thus, a computer on-site is required for the user to access the data. Often, the software is hampered by the operating system, the age of the computer, and/or the particulars of the computer. Computer failings in barns are common, resulting in data loss. Further, fixes for software bugs, when they occur, must be sent to all users. In the systems described herein, the data is accessed on the internet thus eliminating the potential incompatibility of the operating system or computer with the software and minimizing the risk of data loss.

Software

The software can be designed in modules to allow for flexibility and unlimited expansion. Communications can be XML (Extensible Markup Language—a set of rules for representation of arbitrary data structures) based. The software is designed with the ability to access data from any medium, including, for example, websites, local software, and cell phones.

The system is capable of hosting data at a central location while systems can be installed at remote locations without the need to poll the systems locally. Data logging and reporting are not necessarily limited to a single location.

In some embodiments, the software presents raw data to the user. In such cases, the user applies his own standards for determining estrus, e.g. number of mounts in a 2 hour, 3 hour, 4 hour, 5 hour, 6 hour, etc. time period. In other embodiments, the software makes a determination of estrus and then presents the results to the user using, for example, preprogrammed parameters for making estrus determinations. Likewise, the user can screen out the false positives from the raw data presented by the software, or the false positives can be screened out before the results are presented to the user.

Server Module

Server modules can be designed around any one of a number of available platforms, such as, for example, Microsoft's Dot Net platform. The application can be installed on a single machine or multiple servers and has the ability to service an infinite amount of units/clients. In some embodiments, limitations can be imposed by server hardware, storage and interne speeds.

A central location for all data collection utilizes several tested solutions including the following database computer languages designed for managing data in relational database management systems: Microsoft SQL (Structured Query Language), MySQL (My Structured Query Language), and SQLite (embedded). Management includes data query and update, schema creation and modification, and data access control.

Communications can be based on Soap/XML messaging which provides the ability to talk to any system regardless of what platform the system is built upon. SOAP (Simple Object Access Protocol) can form the foundation layer of a web services protocol stack to provide a basic messaging framework upon which to build the estrus detection system. The use of SOAP/XML messaging provides the ability to traverse almost any firewall/network connection as well as the ability to communicate to different versions of clients on a single connection. SOAP/XML can also provide authentication and security to all devices that connect to the server and also provides the ability to run unlimited customers from a single location.

Receiver Module

A hardware based module with built in cellular modems can access any cellular network on the globe through the receiver. The receivers can use the SOAP protocol to enable two way communications with each receiver.

A software based module permits the system to communicate with the older standalone HEATWATCH™ systems as well as the ECHOSTREAM™ design. The software based module permits the system to run as a Window's service in either 32 bit or 64 bit mode: Windows XP, Windows 2000, Windows 2003, Windows Vista, and Windows 7. Simple interfaces can diagnose any attached units. The software based module has the ability to run more than one receiver at a time on a single computer.

EXAMPLE 1

Receiver Module

A Windows-based receiver module can provide a simple interface to set up connection to local or remote servers. Receiver status can be apparent at a glance and a local buffer available in the event the server is unable to be contacted. This ensures messages will not be lost due to an outage. FIG. 12 shows an exemplary receiver setup.

Login Screen

Figure 13:
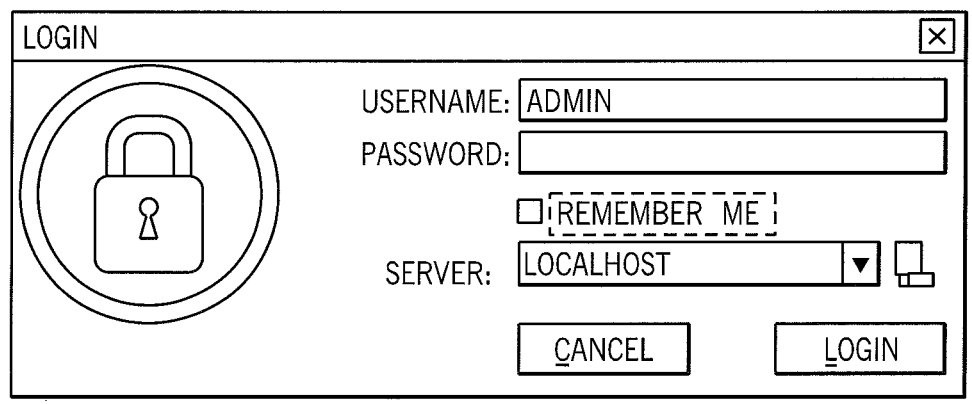
FIG. 13 shows an exemplary login screen in accordance with one embodiment of the present invention.

A login screen allows users to connect to more than one server. Configurations for unlimited systems can be stored in the XML configuration file. FIG. 13 depicts an illustrative login screen.

Windows Client Module

A software based module can run under Unix systems, Windows, or on Macintosh computers, however, in some embodiments the application lacks coding to make a complete system without the server. This set-up prevents a customer from running the system without permission. The server can be administered remotely through the client application and includes limitations on specific information or functions depending on the user permissions.

Figure 14:
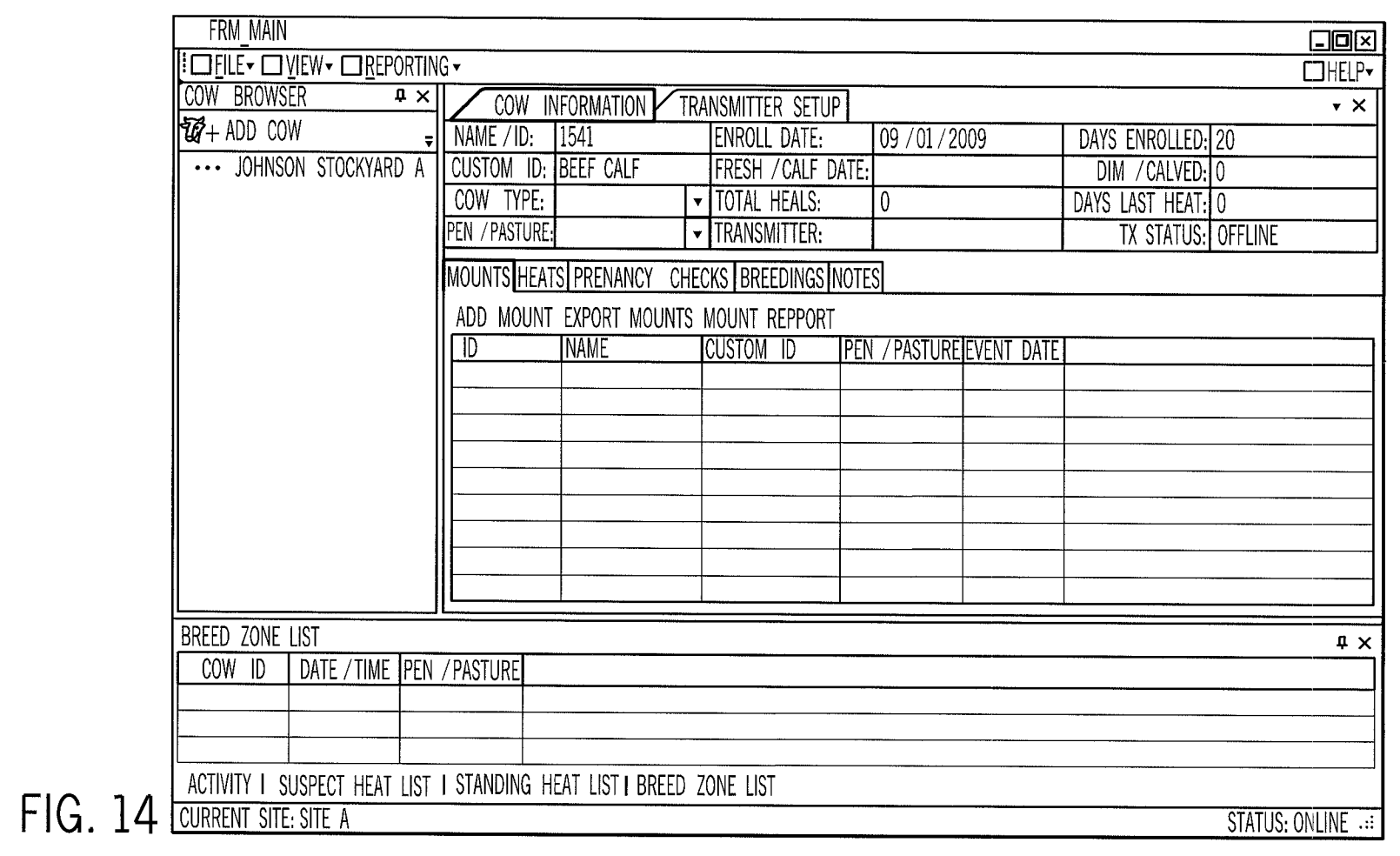
Figure 15:
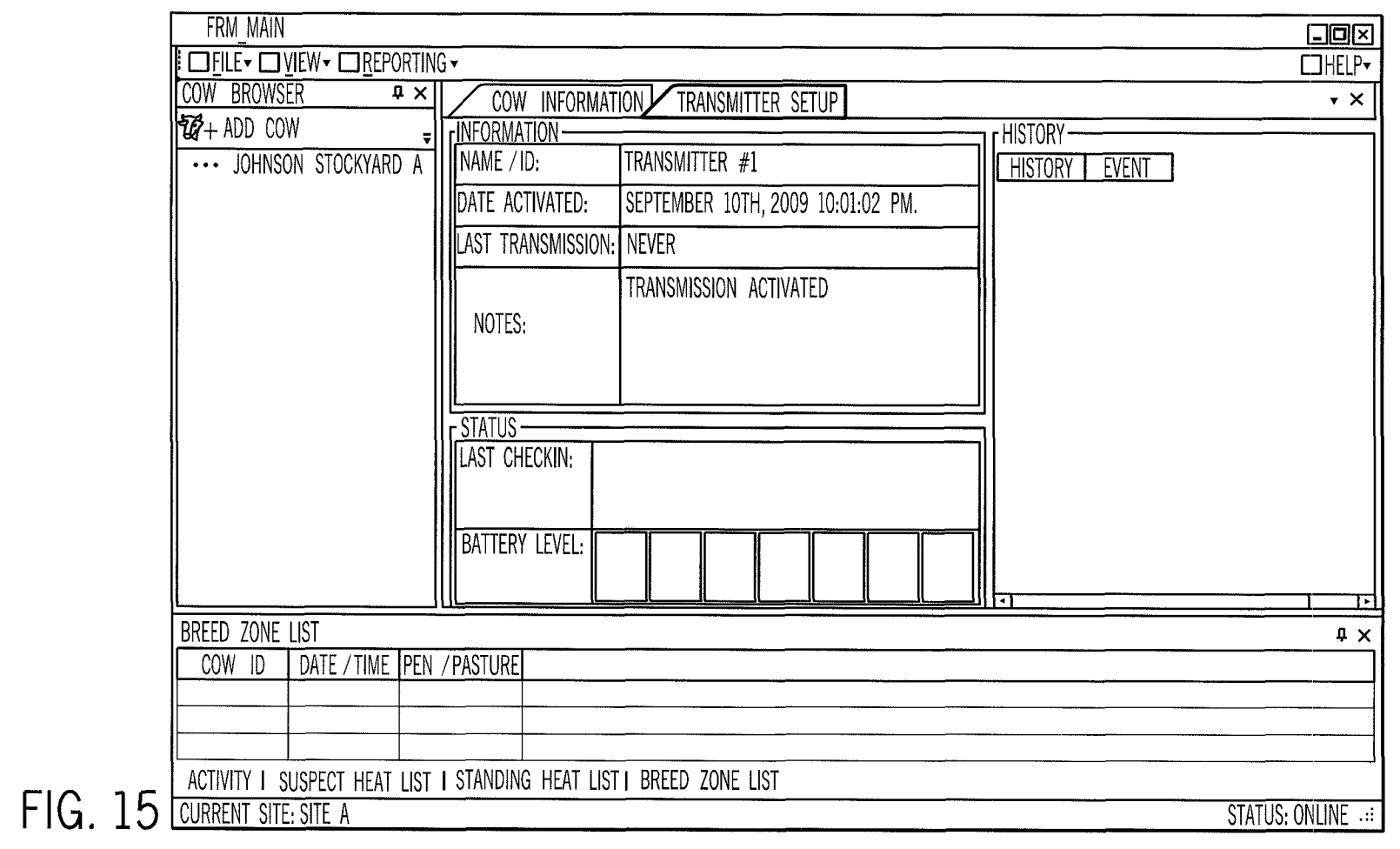

FIG. 14 provides an illustrative main screen with several docked windows, while FIG. 15 exemplifies how a transmitter might be set up in the system.

Figure 16:
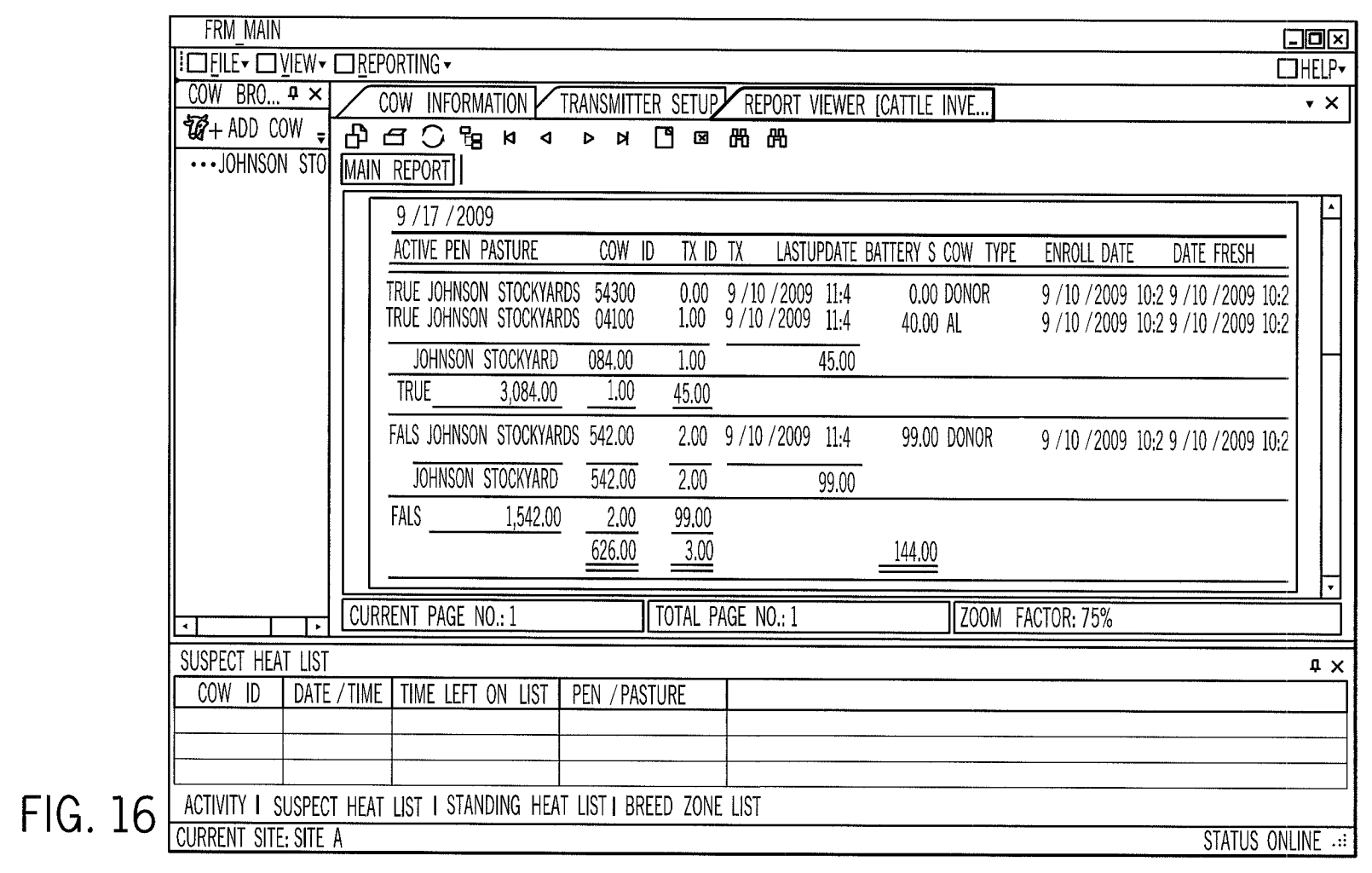

Crystal Reports, a business intelligence application used to design and generate reports from a wide range of data sources, can be used for reporting in a variety of formats including PDF, Word, text, and html. FIG. 16 provides an exemplary report. A simple docking, Windows-style, application allows users to customize the application to their needs. Numbers and dates can be displayed as defined by the user operating the system. Regionalization also includes the ability to set the program to any language, including bidirectional languages such as Hebrew and Arabic.

Cellular Networking—Data

Cellular networking supports data upload through the use of low power cellular modems. A single unit can communicate on GSM or CDMA networks and units maintain low grade data connection to servers via the interne from anywhere. Data is not affected by latency introduced by cellular networks. A signal can be boosted via an external amplifier and a high gain antenna.

EXAMPLE 2

Animal Data

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All publications, published patent documents, and patent applications cited herein are hereby incorporated by reference to the same extent as though each individual publication, published patent document, or patent application was specifically and individually indicated as being incorporated by reference.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiments described and shown in the figures were chosen and described in order to best explain the principles of the invention, the practical application, and to enable others of ordinary skill in the art to understand the invention for various embodiments with various modifications as are suited to the particular use contemplated

The invention claimed is:

1. A system for determining estrus in a female animal, the system comprising:
    (a) a housing adapted for connection to a female animal, the housing enclosing a radio transmitter, a pressure switch, an encoder, an accelerometer, an antenna, and a power supply communicatively connected to each other, wherein the housing is connected to a patch for connection to the female animal, the patch including a stabilization device, and wherein the stabilization device provides a level surface for disposition of the housing at the tailhead of the animal and minimize rocking during mounting activity, the stabilization device having at least two compartments that fit beneath the housing;
    (b) a transceiver comprising a tuner, a power source, an antenna, and a communications link selected from the group of communications links consisting of cellular, RF and Wi-Fi wireless links; and
    (c) a central server;
wherein the data generated by activation of the pressure switch is sent from the transmitter to the transceiver and then from the transceiver to the central server where a determination of estrus is made.

2. The system of claim 1, further comprising one or more repeaters which communicate data between the transceiver and the central server.

3. The system of claim 1, further comprising at least one data entry device, the at least one data entry device being selected from the group of data entry devices consisting of a barcode reader for reading barcode information associated with an animal disposed on a transmitter and an RFI wand for reading RFI identification information associated with an animal disposed on an ear tag or implanted in the animal.

4. The system of claim 1, wherein the transceiver further comprises a decoder.

5. The system of claim 1, wherein the two compartments of the stabilization device are adapted to be disposed on opposing sides of the vertebrae of the animal.

6. The system of claim 1, wherein the housing further encloses a GPS receiver.

7. The system of claim 1, wherein the central server comprises software from which a user can access data compiled by the server.

8. The system of claim 7, wherein the software accesses data from a cellular, RF or Wi-Fi Wireless transmission, a website, other software, or a server.

9. A device for detecting and transmitting a heat mount in a female animal comprising a radio transmitter, a pressure switch, an encoder, an accelerometer, an antenna, and a power supply communicatively connected to each other, and disposed within a hermetically sealed housing adapted to be connected to the female animal, and wherein the housing is connected to a patch for connection to the female animal, the patch including a stabilization device, and wherein the stabilization device provides a level surface for disposition of the housing at the tailhead of the animal and minimize rocking during mounting activity, the stabilization device having at least two compartments that fit beneath the housing.

10. The device of claim 9, further comprising a GPS receiver.

11. The device of claim 9, further comprising a counter, wherein the counter measures the duration of a mount.

12. The device of claim 9, wherein the pressure switch is activated when the female animal is mounted by a mounting animal which generates mounting data.

13. The device of claim 9, wherein the transmitter sends mounting data to a transceiver which sends the mounting data to a central server.

14. The device of claim 9, wherein the accelerometer generates data regarding forward motion of the animal and such data is transmitted to a transceiver which sends the accelerometer data to a central server.

15. The device of claim 14, wherein the accelerometer data indicates whether a standing mount occurred.

16. A method for identifying a female animal in estrus, comprising the steps of:
(a) placing a device comprising a radio transmitter, a pressure switch, an encoder, an accelerometer, an antenna, and a power supply communicatively connected to each other, and disposed within a housing on the tailhead of the female animal, wherein the housing is connected to a patch for connection to the female animal, the patch including a stabilization device, and wherein the stabilization device provides a level surface for disposition of the housing at the tailhead of the animal and minimize rocking during mounting activity, the stabilization device having at least two compartments that fit beneath the housing;
(b) exposing the female animal to a mounting animal;
(c) sensing, through the device, a mount of the female animal by the mounting animal and generating data related to sensing the mount;
(d) transmitting the mount data to a transceiver;
(e) sending the mount data from the transceiver through a cellular link to a central server;
(f) repeating steps (c) through (e) at least once;
(g) processing the mount data using software linked to the central server, wherein the software comprises predetermined parameters for making a determination of estrus; and
(h) accessing the software to determine whether the female animal is in estrus.

17. The method of claim 16, wherein the predetermined parameters include at least three mounts in a three hour period to indicate estrus where estrus begins at the first of the at least three mounts.

18. The method of claim 16, wherein the predetermined parameters include at least three mounts in a four hour period to indicate estrus where estrus begins at the first of the at least three mounts.

19. The method of claim 16, wherein the accessing the software is performed by a cell phone.

20. The method of claim 16, wherein the transmitter is programmed with an identification number for each animal.

21. A method of characterizing the estrus cycle of a particular breed or species of animal, comprising the steps of:
(a) placing a disposable or reusable device comprising a radio transmitter, a pressure switch, an encoder, an accelerometer, an antenna, and a power supply communicatively connected to each other and sealed in a housing on the tailhead of a female animal of the breed or species, wherein the housing is connected to a patch for connection to the female animal, the patch including a stabilization device, and wherein the stabilization device provides a level surface for disposition of the housing at the tailhead of the animal and minimize rocking during mounting activity, the stabilization device having at least two compartments that fit beneath the housing;
(b) exposing the female animal to a mounting animal;
(c) sensing through the device a mount of the female animal by the mounting animal and generating data related to sensing the mount;
(d) transmitting the mount data to a transceiver;
(e) sending the mount data from the transceiver through a cellular, RF, Wi-Fi Wireless or combination link to a central server;
(f) repeating steps (c) through (e) at least once;
(g) accessing the mount data using software linked to the central server;
(h) making a determination of whether the female animal is in estrus based on the data; wherein the steps (c) through (h) are repeated over about 2 weeks to about 2 years to characterize the estrus cycle; and
(i) correlating the determination of estrus to the breed or species of animal and thereby characterizing the estrus cycle of the breed or species.

22. The system of claim 5, wherein the compartments are filled with sand or other weighted material.

23. The system of claim 1, further comprising a strap attached to the patch to facilitate removal of the patch from the animal.

24. The system of claim 9, wherein the two compartments of the stabilization device are adapted to be disposed on opposing sides of the vertebrae of the animal and wherein the two compartments are filled with sand or other weighted material.

25. The system of claim 9, further comprising a strap attached to the patch to facilitate removal of the patch from the animal.

* * * * *